United States Patent
Green

(10) Patent No.: US 8,224,629 B2
(45) Date of Patent: Jul. 17, 2012

(54) METHOD OF MODELLING A SATURATION DEPENDANT PROPERTY IN A SAMPLE

(75) Inventor: Derrick Green, Fredericton (CA)

(73) Assignee: Green Imaging Technologies, Inc., Fredericton (CA)

( * ) Notice: Subject to any disclaimer, the term of this patent is extended or adjusted under 35 U.S.C. 154(b) by 810 days.

(21) Appl. No.: 12/208,120

(22) Filed: Sep. 10, 2008

(65) Prior Publication Data

US 2009/0228249 A1      Sep. 10, 2009

Related U.S. Application Data

(60) Provisional application No. 60/935,974, filed on Sep. 10, 2007.

(51) Int. Cl.
*G06F 7/60* (2006.01)
*G06F 17/10* (2006.01)

(52) U.S. Cl. .................. 703/2; 703/9; 324/303; 702/6

(58) Field of Classification Search .................. 703/2, 9, 703/10; 324/303; 702/6
See application file for complete search history.

(56) References Cited

U.S. PATENT DOCUMENTS

| 6,008,645 | A | * | 12/1999 | Bowers et al. | ................. 324/303 |
| 7,352,179 | B2 |   | 4/2008 | Chen et al. | |
| 7,567,079 | B2 |   | 7/2009 | Chen et al. | |
| 7,623,988 | B2 | * | 11/2009 | Bedard et al. | ................. 702/189 |
| 2003/0094946 | A1 | * | 5/2003 | Galford et al. | ................. 324/303 |
| 2006/0116828 | A1 | * | 6/2006 | Chen et al. | ...................... 702/22 |
| 2006/0273788 | A1 | * | 12/2006 | Georgi et al. | ................... 703/10 |

OTHER PUBLICATIONS

Chen et al. Advances in Water Resources vol. 22, No. 5., "Parameter estimation of two-fluid capillary pressure-saturation and permeability functions"., 1998. p. 479-493.*

D. Ruth and Z. Chen, "The Log Anayst" 36, 21 (1995), "Measurement and Interpretation of Centrifuge Capillary Pressure Curves—The SCA Survey Data", 13 Pgs.

Hassler, G. L ., Brunner, E., "Measurement of Capillary Pressure in Small Core Samples", Trans AIME, 1945, 160, 114-123.

N. T. Burdine, Trans. AIME 198, 71 (1953) , "Relative Permeability Calculations From Pore Size Distribution Data", 8 Pages.

(Continued)

*Primary Examiner* — Mary C Jacob
*Assistant Examiner* — Eunhee Kim
(74) *Attorney, Agent, or Firm* — Eugene F. Derényi; Fogler, Rubinoff LLP

(57) ABSTRACT

A method for modelling a saturation dependant property in a sample by obtaining a spatially resolved measurement of fluid saturation in the sample; determining a measured value of a saturation dependant property from the measurement; fitting a model to the measured value to obtain a model value for the measured value; and optimising the fit of the model to the measured value by minimizing an error between the model and the measured value where the error is a distance between the measured value and the model value.

5 Claims, 4 Drawing Sheets

OTHER PUBLICATIONS

Van Genuchten, M. T. A Closed-form Equation for Predicting the Hydraulic Conductivity of Unsaturated Soils:, Soil Sci. Soc. Am J., 44, 892-298 (1990).

Brooks, RH, Corey, AT, "Hydraulic Properties of Porous Media" Hydrol. Pap, 3, Colo. State Univ., Fort Collins (1964)

Leverett M., "Capillary Behaviour in Porous Solids", Trans. AIME (1941), 142, 152.

Brown H. W., "Capillary Pressure Investigations", Trans AIME, (1951), 192, 62.

Balcom, B. J. et al "Bindle Point Ramped imaging with T1 Enhancement (SPRITE)", J. Magn. Res. A (1996) 123, 131-134.

Chen Q. et al. "A Magnetic Resonance Study of Pore Filling Processes During Spontaneous Imbibition in Berea Sandstone", J. Chem. Phys., 119, 9609-9616 (2003).

Balcom, B. J. et al. "Single-point Magnetic Resonance Imaging (MRI) of Cement Based Materials", (2003) 36, 166-182.

* cited by examiner

METHOD OF MODELLING A SATURATION DEPENDANT PROPERTY IN A SAMPLE

CROSS-REFERENCE TO RELATED APPLICATIONS

This application claims the benefit of U.S. provisional patent application Ser. No. 60/935,974 filed on Sep. 10, 2007.

BACKGROUND OF THE INVENTION

Capillary pressure curves are widely used in material, soil and environmental sciences, and especially in the petroleum industry. Capillary pressure curves provide critical information frequently used in the assessment of the economic viability of oil reservoir development.

Capillary pressure may be obtained by either mercury intrusion, porous plate, or centrifuge methods. The mercury intrusion method is rapid, but it is destructive, and the mercury/vacuum system does not represent the wettability of reservoir system. The porous plate method is a direct and accurate technique, but is extremely time-consuming, since the equilibrium time can range from a week to months per pressure point.

The centrifugal capillary pressure curve technique was introduced by Hassler and Brunner in 1945, as described in Hassler, G. L., Brunner, E., "Measurement of Capillary Pressure in Small Core Samples", Trans. AIME, 1945, 160, 114-123 and N. T. Burdine, Trans. AIME 198, 71 (1953) which is incorporated herein by reference. This technique, which involves rotating fluid bearing rock cores at variable speeds in a specially modified centrifuge, has been extensively investigated, and is commonly used in the petroleum industry. Sample rotation yields a centrifugal force which will empty pores with matching capillary forces. Collecting the expelled fluid as a function of increasing rotational speed permits a quantification of the capillary pressure as a function of fluid content or saturation.

The Hassler-Brunner centrifugal capillary pressure technique, which involves rotating fluid bearing rock cores at variable speeds in a specially modified centrifuge, has been extensively investigated, and is commonly used in the petroleum industry. Sample rotation yields a centrifugal force which will empty pores with matching capillary forces. Collecting the expelled fluid as a function of increasing rotational speed permits a quantification of the capillary pressure as a function of fluid content or saturation.

The conventional interpretation of centrifugal capillary pressure data is based on several assumptions: (1) nonlinearity of the centrifugal field is not significant; (2) gravity has no effect on fluid distribution; and (3) the capillary pressure is zero at the bottom (outlet end-face) of the core plug. These assumptions are known to lead to significant errors in the measurement of the capillary pressure curve. In addition, these three conditions can not be simultaneously satisfied. The first assumption requires a short sample and large rotational radius. For low capillary pressures, the experiment requires a very low rotational speed. In this case, the effect of gravity can not be neglected. For high capillary pressures, the experiment requires a very high rotation speed, which is likely to lead to a violation of the third assumption (capillary pressure is zero at the outlet). In addition, the rock pore structure in unconsolidated or friable samples (for example marginal reservoirs) will change due to the high centrifugal forces, thereby altering the capillary pressure curve.

Conventional centrifuge methods for capillary pressure determination are time consuming and special instrumentation is required for the experiment. Measurement of the full capillary pressure curve requires approximately 15 different centrifuge speeds, thus requiring one day to several days for measurement. In addition, some friable and unconsolidated rock samples may be broken during ultracentrifugation, as described in D. Ruth and Z. Chen, The Log Analyst 36, 21 (1995). The experiment requires a very expensive ultracentrifuge with precise speed control over a wide range of speeds. A special core holder and stroboscope for collecting and measuring expelled liquid are also necessary for the experiment.

Magnetic Resonance Imaging (MRI) can also be used for capillary pressure determination. NMR is a powerful, non-destructive, measurement method, which, with techniques developed by the inventors described in Balcom, B. J., MacGregor, R. P., Beyea, S. D., Green, D. P., Armstrong, R. L. and Bremner, T. W. "Single Point Ramped Imaging with T1 Enhancement (SPRITE)", J. Magn. Res. A (1996) 123, 131-134, offer unique advantages in the measurement of spatially resolved fluid saturation in porous media, discussed in Chen, Q., Gingras, M. and Balcom, B. J., "A magnetic resonance study of pore filling processes during spontaneous imbibition in Berea sandstone", J. Chem. Phys., 119, 9609-9616 (2003) and Balcom, B. J., Barrita, J. C., Choi, C., Beyea, S. D., Goodyear, D. J. and Bremner, T. W. "Single-point magnetic resonance imaging (MRI) of cement based materials", Materials and Structures (2003) 36, 166-182.

Capillary pressure measurements can be obtained through the use of a centrifuge and MRI equipment as described in U.S. Pat. No. 7,352,179 which is incorporated herein by reference (hereinafter referred to as "GIT-CAP"). To fully measure the capillary pressure curve, several centrifuge speeds (typically 3 to 5) are required.

For example, FIG. 1 illustrates a capillary pressure curve acquired with measures obtained using 5 centrifuge speeds. The solid line in the plot of FIG. 1 is the conventionally (centrifuge only) acquired capillary pressure curve. The data points in the different centrifuge speeds Pc cover different portions of the Pc curve and can be acquired according to one or more of the GIT-CAP methods. One set of data points from a single speed alone does not fully define the Pc curve but it is enough information to fulfill a Pc model that would fully define the curve.

Another saturation dependant measurement is relative permeability. Relative permeability describes the flow of one fluid or gas at different saturation levels of another fluid or gas. The flow rate at 0% level of the other fluid/gas is 1.0 by definition. One method of obtaining relative permeability using MRI equipment is described in U.S. patent application Ser. No. 11/808,300 filed on Jun. 8, 2007, which is incorporated herein by reference.

Conventional Capillary Pressure Models

Capillary pressure models exist for modelling capillary pressure curves using capillary pressure measurements obtained from conventional methods (other than MRI). The two most popular are the Brooks-Corey (Brooks, R H, Corey, A T, "Hydraulic properties of porous media" Hydrol. Pap., 3, Colo. State Univ., Fort Collins (1964)) and the van Genuchten (van Genuchten, M. T. "A Closed-form equation for predicting the hydraulic conductivity of unsaturated soils", Soil Sci. Soc. Am. J., 44, 892-298 (1990)) models which are incorporated herein by reference. The Brooks-Corey model uses the residual water saturation and therefore in cases where it is known may provide a better fit. After selecting a model, the least squares fit is applied to fit the model parameters.

Brook-Corey Pc Model

The Brooks-Corey model relates capillary pressure and water saturation as:

$$P_C = p_e(S_W^*)^{-\frac{1}{\lambda}} \quad (1)$$

Where $p_e$ and $\lambda$ are fitted parameters, $P_C$ is the normalized wetting-phase (water for air water) saturation and is defined as follows:

$$S_w^* = \frac{S_w - S_{wr}}{1 - S_{wr}} \quad (2)$$

Where $S_w$ is the water saturation and $S_{wr}$ is the residual water saturation. Substituting (2) in (1) and rearranging for $S_w$ we get:

$$S_W = (1 - S_{wr})\left(\frac{P_C}{P_e}\right)^{-\lambda} + S_{wr} \quad (3)$$

van Genuchten Pc Model

The van Genuchten model related Pc and water saturation as:

$$P_C = \frac{1}{\alpha}\left(S_w^{-\frac{1}{M}} - 1\right)^{\frac{1}{N}} \quad (4)$$

Where $P_C$ is the capillary pressure, $S_w$ is the water saturation and $\alpha$, M and N are fit parameters where N and M are related by:

$$N = \frac{1}{1 - M} \quad (5)$$

Substituting equation (5) into (4) and rearranging for $S_w$ gives:

$$S_w = (1 + (\alpha P_C)^N)^{-\frac{N-1}{N}} \quad (6)$$

Least Fit Error

There a many ways to calculate the model error and then minimize that error to find the optimal solution (fit). The simplest error is the summation of the difference between the measured Y value and the calculated (modelled) Y value squared as described in:

$$\text{Error} = \Sigma(S_{w-measured} - S_{w-calculated})^2$$

This will place equal weighting on all Y values and assumes the X values have little or no error. This works well for linear data (i.e. y=mx+b). For capillary pressure curve data the data is not linear and is exponential in nature. A better error equation is the percentage change in the Y values.

$$\text{Error} = \sum\left(\frac{S_{w-measured} - S_{w-calculated}}{S_{w-measured}}\right)^2 \quad (8)$$

This places a 1/X weighting on the error putting more importance on the Y values that are closer to X=0 (lower saturations). This produces a better fit for Pc data. The error in saturation units is lower at lower saturation values.

BRIEF DESCRIPTION OF THE DRAWING

The invention is described below in greater detail with reference to the accompanying drawings.

DESCRIPTION OF THE INVENTION

Figure 1:
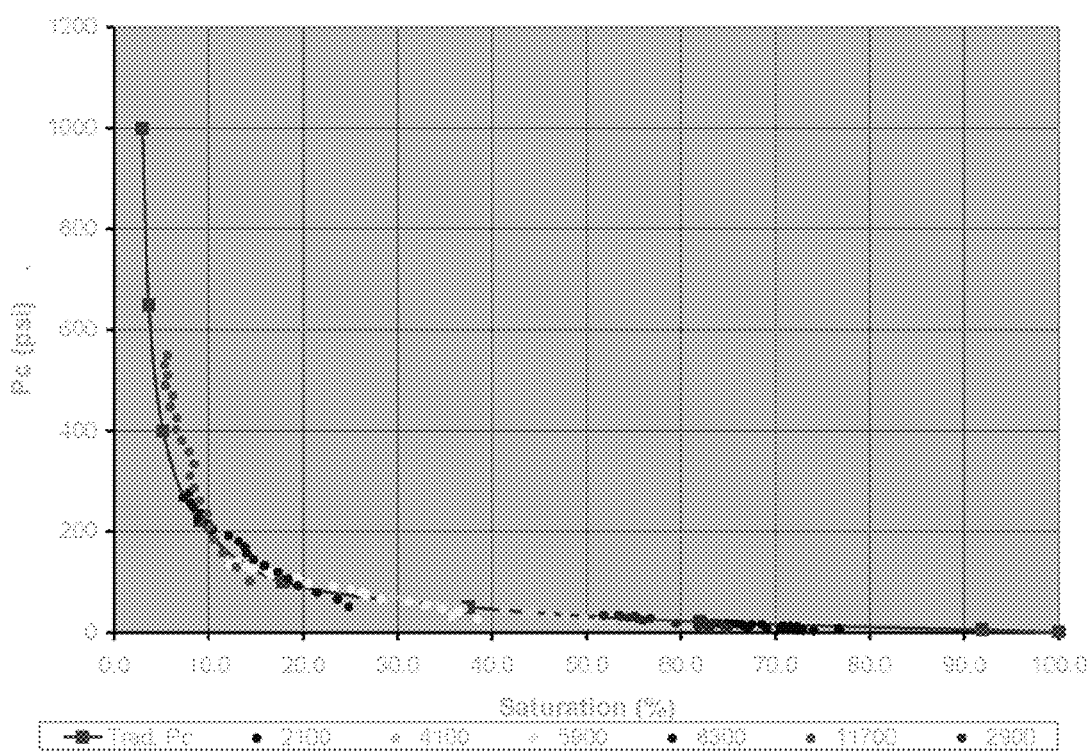
FIG. 1 is a capillary pressure curve acquired with measures obtained using 5 centrifuge speeds.

According to the present invention, there is provided a method for modelling a saturation dependant property in a sample comprising the steps of obtaining a spatially resolved measurement of fluid saturation in the sample using an external force; determining a measured value of a saturation dependant property from the measurement; fitting a model to the measured value to obtain a model value for the measured value; and optimising the fit of the model to the measured value by minimizing an error between the model and the measured value where the error is a distance between the measured value and the model value.

According to the present invention, there is provided a method of modelling a capillary pressure curve comprising: providing a capillary measurement, and modelling a capillary pressure curve based on said measurement. The capillary pressure measurement may be obtained using a centrifuge method using a single centrifuge speed. The capillary pressure measurement may be a direct measurement of water saturation. The water saturation measurement may be obtained using magnetic resonance imaging.

Also according to the present invention, there is provided a method of modelling a capillary pressure curve comprising: providing a capillary pressure measurement obtained using a centrifuge method using a single centrifuge speed; modelling a capillary pressure curve based on said measurement. The Brook-Corey Pc Model or the van Genuchten Pc model may be used to model said pressure curve. A least squares fit may be used to fit the model parameters.

Also according to the present invention, there is provided a method of generating capillary pressure values for a sample comprising: obtaining a water saturation measurement for said sample by a centrifuge method at a single centrifuge rotational speed, generating additional water saturation values using a capillary pressure model using said water saturation measurement, adjusting the generated additional saturation values. A conventional capillary pressure model, including the Brook-Corey Pc Model and the van Genuchten Pc Model, may be used to generate said additional water saturation valves. The generated additional saturation valves may be adjusted using a conventional adjustment technique including least squares adjustment.

The adjusted generated additional saturation valves may be used to generate a capillary pressure curve.

In one embodiment, the present invention relates to a method of the acquiring or modelling complete capillary pressure curves using capillary measurements obtained using only a single (equilibrium) centrifuge speed. The capillary pressure curve is modelled using an equation and fitting the measured data and is up to 5 times faster than capillary pressure curves obtained using the methods of U.S. Pat. No. 7,352,179, and faster still than other conventional methods.

In one embodiment, the method of the present invention uses direct measurement data of the water saturation of a sample obtained using magnetic resonance imaging thus eliminating the complex modeling required for conventional centrifuge measurement.

Figure 4:
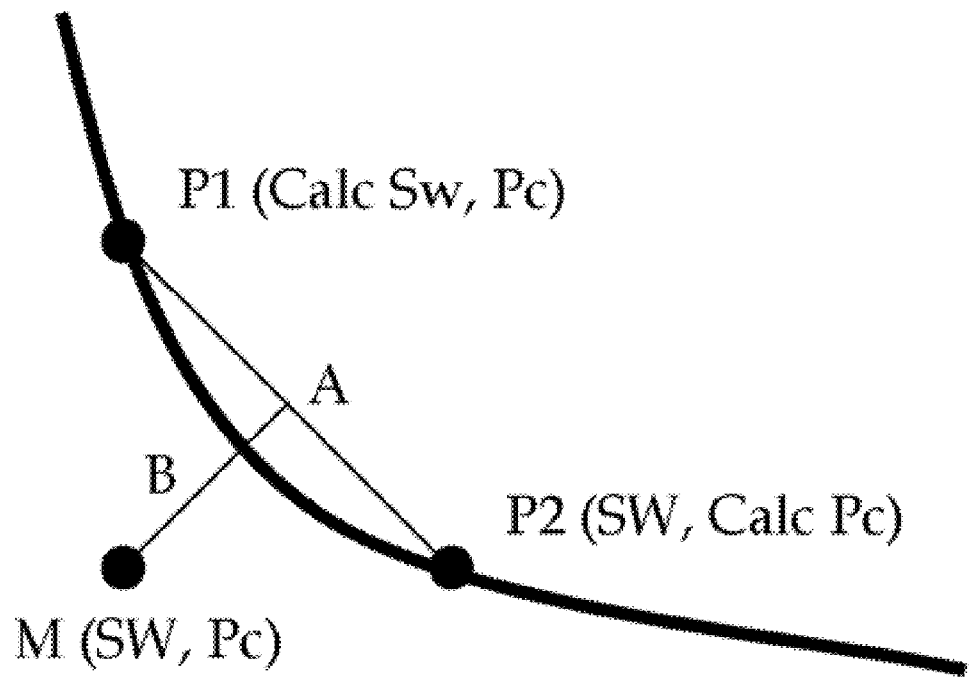
FIG. 4 is a graphical representation of error minimization according to the present invention.

In another embodiment, an error function which minimizes the distance of the line A on FIG. 4 can be used to model a capillary pressure curve. The error function is given by the following equation:

$$\text{Error} = \Sigma\{(S_{w-measured} - S_{w-calculated})^2 + (P_{C-measured} - P_{C-calculated})^2\} \quad (9)$$

To normalize for the numbers one must divide by full scale X and Y axis values to obtain:

$$\text{Error} = \sum \left\{ \left(\frac{S_{w-measured} - S_{w-calculated}}{S_{w-FullScale}}\right)^2 + \left(\frac{P_{C-measured} - P_{C-calculated}}{P_{C-FullScale}}\right)^2 \right\} \quad (10)$$

where $S_{w-measured}$ is the measured water saturation, $S_{w-calculated}$ and $P_{c-calculated}$ are the calculated water saturation and capillary pressure from the modeled equation, $S_{W-Fullscale}$ is maximum measured water saturation (usually 100%) and $P_{c-Fullscale}$ is the maximum measured capillary pressure.

$S_{w-Full\ Scale}$ at 100% and $P_{c-Full\ Scale}$ at maximum measured PSI 1000 PSI was used in the examples below.

In another embodiment, another error function which minimizes the distance from the measured point to the calculated curve along a line that is at right angles to the calculated curve can be used. The length of line B in FIG. 4 can be minimized to provide a good approximation. In this case the error equation is:

$$\text{Error} = \sum \left\{ \frac{(S_{w-measured} - S_{w-calculated})^2 (P_{C-measured} - P_{C-calculated})^2}{(S_{w-measured} - S_{w-calculated})^2 + (P_{C-measured} - P_{C-calculated})^2} \right\} \quad (11)$$

To normalize for the numbers one must divide by full scale X and Y axis values to obtain:

$$\text{Error} = \sum \left\{ \frac{\left(\frac{S_{w-measured} - S_{w-calculated}}{S_{w-FullScale}}\right)^2 \left(\frac{P_{C-measured} - P_{C-calculated}}{P_{C-FullScale}}\right)^2}{\left(\frac{S_{w-measured} - S_{w-calculated}}{S_{w-FullScale}}\right)^2 + \left(\frac{P_{C-measured} - P_{C-calculated}}{P_{C-FullScale}}\right)^2} \right\} \quad (12)$$

where $S_{w-measured}$ is the measured water saturation, $S_{w-calculated}$ and $P_{c-calculated}$ are the calculated water saturation and capillary pressure from the modeled equation, $S_{w-Fullscale}$ is maximum measured water saturation (usually 100%) and $P_{c-Fullscale}$ is the maximum measured capillary pressure.

$S_{w-Full\ Scale}$ is 100% and $P_{c-Full}$ Scale is 1000 PSI in the examples below.

EXAMPLES

Figure 2:
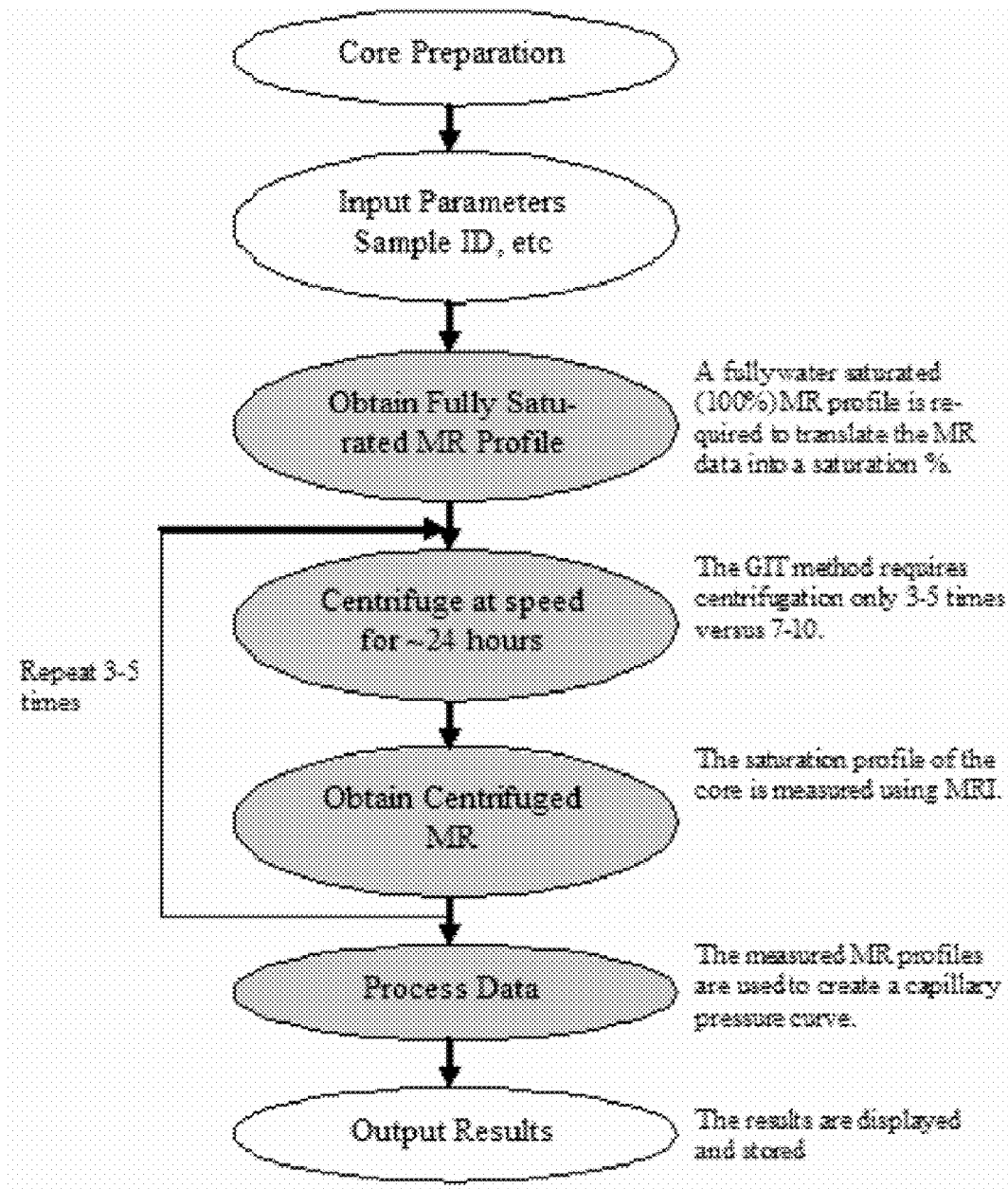
FIG. 2 is a flow chart of the GIT-CAP process.

GIT-CAP acquired data was fitted to the two models listed above. In addition, each of the four error functions described above were used creating 8 model fits for each GIT-CAP centrifuge speed. A quantitative evaluation of the data was performed to determine the best model and error function. GIT-CAP data was acquired using the method summarized in the flow chart of FIG. 2.

Figure 3:
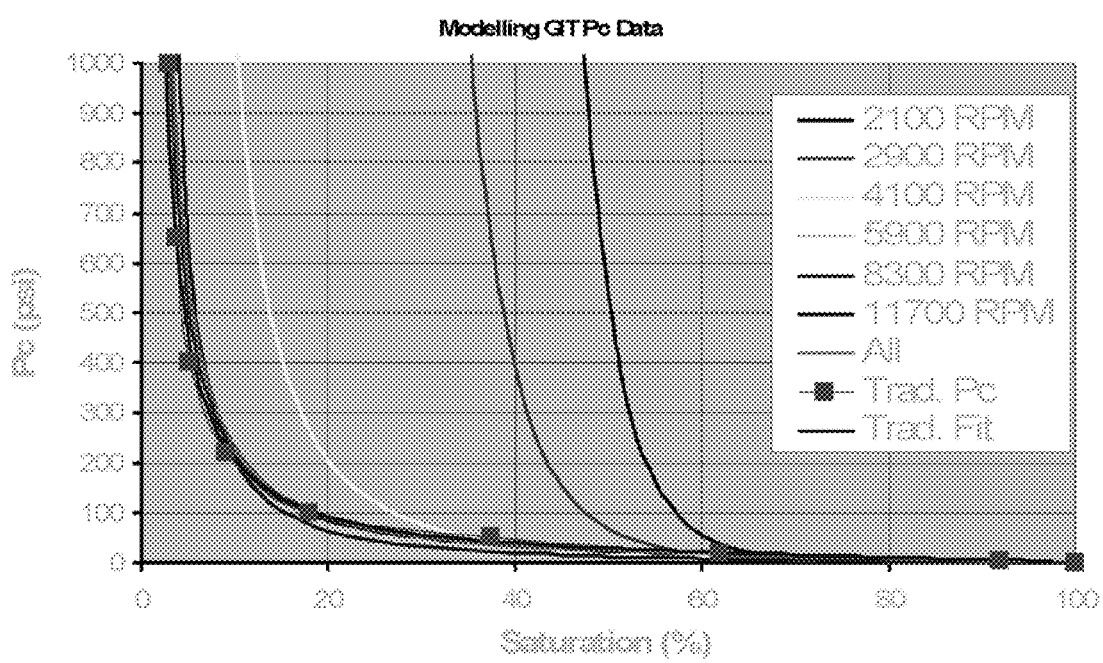
FIG. 3 is a graph showing modelling of $P_C$ data.

Fits were performed for various rock samples using: 1) each centrifuge speed for the GIT-CAP acquired data 2) all the centrifuge speeds together, and 3) the conventionally acquired centrifuge data. See FIG. 3.

Table 1 sets out the fit parameters for a curve fitted using van Genuchten Pc modelling.

TABLE 1

| | van Genuchten Model parameters for the various centrifuge speeds. | | | | | | | |
|---|---|---|---|---|---|---|---|---|
| Pc (PSI) | 2100 RPM J = 0.5 | 2900 RPM J = 1.0 | 4100 RPM J = 2.0 | 5900 RPM J = 4.0 | 8300 RPM J = 8.0 | 11700 RPM J = 16.0 | All RPM | Trad. Fit |
| Alpha | 9.34 | 3.35 | 0.23 | 0.09 | 0.09 | 0.23 | 0.09 | 0.07 |
| M | 1.08 | 1.13 | 1.42 | 1.75 | 1.77 | 1.60 | 1.75 | 1.86 |
| N | 0.08 | 0.11 | 0.29 | 0.43 | 0.43 | 0.37 | 0.43 | 0.46 |

The fitted results were analyzed by comparing the van Genuchten modelled fit to the values obtained by the conventional centrifuged capillary pressure as a base line. The following Table 2 shows the difference in saturation value (in pu) from the conventional centrifuge values. A more accurate analysis may be to compare the single speed fits to the fit produced by all the centrifuge speeds combined.

TABLE 2

| | van Genuchten model saturation error in p.u. from conventional centrifuge data | | | | | | | |
|---|---|---|---|---|---|---|---|---|
| Pc (PSI) | 2100 RPM J = 0.5 | 2900 RPM J = 1.0 | 4100 RPM J = 2.0 | 5900 RPM J = 4.0 | 8300 RPM J = 8.0 | 11700 RPM J = 16.0 | All RPM | Trad. Fit |
| 1000 | 44.4 | 32.4 | 7.4 | 0.4 | 0.1 | 0.9 | 0.3 | −0.4 |
| 650 | 45.4 | 33.7 | 8.7 | 1.0 | 0.6 | 1.4 | 0.9 | 0.0 |
| 400 | 45.8 | 34.6 | 10.0 | 1.5 | 1.0 | 1.6 | 1.4 | 0.5 |
| 220 | 44.6 | 34.0 | 10.5 | 1.5 | 0.8 | 0.6 | 1.4 | 0.5 |
| 100 | 39.3 | 29.7 | 9.1 | 0.8 | 0.0 | −2.5 | 0.7 | 0.7 |
| 50 | 23.0 | 14.5 | −1.7 | −6.7 | −7.6 | −14.4 | −6.7 | −4.7 |

TABLE 2-continued van Genuchten model saturation error in p.u. from conventional centrifuge data

| Pc (PSI) | 2100 RPM J = 0.5 | 2900 RPM J = 1.0 | 4100 RPM J = 2.0 | 5900 RPM J = 4.0 | 8300 RPM J = 8.0 | 11700 RPM J = 16.0 | All RPM | Trad. Fit |
|---|---|---|---|---|---|---|---|---|
| 20 | 3.2 | −3.6 | −10.7 | −6.6 | −7.2 | −23.0 | −6.4 | −0.2 |
| 5 | −19.0 | −22.5 | −12.7 | −1.5 | −1.4 | −18.1 | −1.3 | 2.3 |
| 0 | 0.0 | 0.0 | 0.0 | 0.0 | 0.0 | 0.0 | 0.0 | 0.0 |

Table 3 sets out the fit parameters for a curve fitted using Brooks-Corey modelling.

TABLE 3

Brooks-Corey model results for various centrifuge speeds

|  | 2100 | 2900 | 4100 | 5900 | 8300 | 11700 | All RPM | Trad. Fit |
|---|---|---|---|---|---|---|---|---|
| Lamda | 0.08 | 0.13 | 0.36 | 0.66 | 0.79 | 0.68 | 0.59 | 0.89 |
| Pe | 0.11 | 0.29 | 2.95 | 8.10 | 11.20 | 7.41 | 4.80 | 12.43 |
| Swr | 0.00 | 0.00 | 0.00 | 0.00 | 0.00 | 0.00 | 0.00 | 0.96 |

TABLE 4

Brooks-Corey model saturation error in p.u. from conventional centrifuge data

| Pc (PSI) | 2100 | 2900 | 4100 | 5900 | 8300 | 11700 | All RPM | Trad. Fit |
|---|---|---|---|---|---|---|---|---|
| 1000 | 44.4 | 32.5 | 9.5 | 1.1 | −0.1 | 0.6 | 1.2 | −0.1 |
| 650 | 45.4 | 33.8 | 10.9 | 1.7 | 0.4 | 1.1 | 1.7 | 0.2 |
| 400 | 45.9 | 34.7 | 12.2 | 2.3 | 0.8 | 1.5 | 2.1 | 0.3 |
| 220 | 44.6 | 34.0 | 12.5 | 2.2 | 0.6 | 1.0 | 1.4 | −0.4 |
| 100 | 39.3 | 29.7 | 10.6 | 0.9 | −0.1 | −0.8 | −1.4 | −1.5 |
| 50 | 23.0 | 14.5 | −1.1 | −7.7 | −6.8 | −10.1 | −12.6 | −7.9 |
| 20 | 3.2 | −3.6 | −11.5 | −7.1 | 1.3 | −11.0 | −19.1 | 3.8 |
| 5 | −18.8 | −22.2 | −9.1 | 8.1 | 8.1 | 8.1 | 5.7 | 8.1 |
| 0.001 | 0.0 | 0.0 | 0.0 | 0.0 | 0.0 | 0.0 | 0.0 | 0.0 |

Table 5 below summarizes the tests performed with a column indicating the best model. In all cases the error function described by equation (10) proved to yield the best results.

TABLE 5

Summary of different rocks modeled

| Sample | Porosity (p.u.) | Permeability (mD) | Best Result |
|---|---|---|---|
| 6A | 14.9 | 10.7 | Van Genuchten |
| 1A | 25.8 | 13.3 | Van Genuchten |
| 17 | 12.6 | 1.08 | Brooks-Corey |
| 30 | 12.8 | 2.32 | Brooks-Corey |
| 31 | 14.5 | 2.28 | Van Genuchten |
| 34 | 14.5 | 0.908 | Van Genuchten |

Both the Brooks-Corey and van Genuchten models produced similar results. The Brook-Corey model proved more unstable at lower centrifuge speeds but did fit the data better in cases where there was an entry pressure. The models produced results that were accurate within 10 saturation units. The errors were more pronounced at lower capillary pressures where the saturation is changing more rapidly. The error function described by equation (10) consistently produced the best fits. This is due to the fact that it equally weights the x and y axis and does not assume linearity in the data. This error does however overly weight the start and end of the Pc curve (unweighting the "knee" of the curve). The best solution is the error described by equation 12.

Rotational speed for the centrifuge can be determined by using the following equation, known as the Leverett J function Leverett M., "Capillary behaviour in porous solids", Trans. AIME, (1941), 142, 152.

$$P_c(r) = 1/2\Delta\rho\omega^2(r_2^2 - r_1^2) \geq \frac{J(S_{wi})\sigma\cos\theta}{\sqrt{\frac{k}{\phi}}} \quad (14)$$

where J is the Leverett value, $\sigma$ is the normal interfacial tension, $\theta$ is the contact angle, k is the permeability and $\phi$ is the porosity for a given rock. The J value "normalizes" the speed using this function Brown H. W., "Capillary pressure investigations", Trans. AIME, (1951), 192, 67. RPM speeds that produced J factors of between 4 and 8 had consistent results (sometimes J factors of 2 were good as well). To produce a model single speed curve as described here it is suggested to use a centrifuge speed that produces a J factor of 4 for any model.

The signal to noise ratio (SNR) of the underlying MRI scan will affect the accuracy of the resultant fit using any model. Various SNR ratios were investigated and it is suggested for single speed test that the SNR be at least 200. This produces variations in the data of less than five saturation units.

It will be understood by those skilled in the art that the modelling methods described here can be used to model capillary pressure curves using capillary measurement data acquired using both conventional centrifuge methods and the GIT-CAP methods.

REFERENCES

U.S. patent application Ser. No. 11/262,658, "Methods and apparatus for measuring capillary pressure in a sample".
Van Genuchten, M. T. "A Closed-form equation for predicting the hydraulic conductivity of unsaturated soils", Soil Sci. Soc. Am. J., 44, 892-298 (1990)
Brooks, R H, Corey, A T, "Hydraulic properties of porous media" Hydrol. Pap., 3, Colo. State Univ., Fort Collins (1964)
Leverett M., "Capillary behaviour in porous solids", *Trans. AIME*, (1941), 142, 152.
Brown H. W., "Capillary pressure investigations", *Trans. AIME*, (1951), 192, 67.

I claim:
1. A method for modeling a saturation dependant property in a sample, wherein the property is selected from the group consisting of capillary pressure and relative permeability, the method comprising the steps of:
    (a) obtaining a spatially resolved measurement of fluid saturation in the sample using an external force;
    (b) determining a measured value of a saturation dependant property from the measurement;
    (c) fitting a model to the measured value to obtain a model value for the measured value;
    (d) optimizing the fit of the model to the measured value by minimizing an error between the model and the measured value where the error is a distance between the measured value and the model value, wherein the error is modeled by the following equation:

$$\text{Error} = \sum \left\{ \left(\frac{S_{w-measured} - S_{w-calculated}}{S_{w-FullScale}}\right)^2 + \left(\frac{P_{C-measured} - P_{C-calculated}}{P_{C-FullScale}}\right)^2 \right\}$$

where $S_{w-measured}$ is measured water saturation, $S_{w-calculated}$ and $P_{c-calculated}$ are calculated water saturation and capillary pressure from a capillary pressure model equation, $S_{w-Fullscale}$ is maximum measured water saturation,
$P_{c-measured}$ is measured capillary pressure and
$P_{c-Fullscale}$ is maximum measured capillary pressure; and
(e) repeating step (d).

2. The method according to claim 1 wherein the error is modeled by the following equation:

$$\text{Error} = \sum \left\{ \frac{\left(\frac{S_{w-measured} - S_{w-calculated}}{S_{w-FullScale}}\right)^2 \left(\frac{P_{C-measured} - P_{C-calculated}}{P_{C-FullScale}}\right)^2}{\left(\frac{S_{w-measured} - S_{w-calculated}}{S_{w-FullScale}}\right)^2 + \left(\frac{P_{C-measured} - P_{C-calculated}}{P_{C-FullScale}}\right)^2} \right\}$$

where $S_{w-measured}$ is measured water saturation, $S_{w-calculated}$ and $P_{c-calculated}$ are calculated water saturation and capillary pressure from a capillary pressure model equation, $S_{w-Fullscale}$ is maximum measured water saturation, $P_{c-measured}$ is measured capillary pressure and $P_{c-Fullscale}$ is maximum measured capillary pressure.

3. The method according to claim 2 where the external force is applied before the spatial resolved measurement using a centrifuge.

4. The method according to claim 1 wherein the capillary pressure model equation is selected from the group consisting of a Brook-Corey Pc Model and a van Genuchten Pc Model.

5. The method according to claim 2 wherein the capillary pressure model equation is selected from the group consisting of a Brook-Corey Pc Model and a van Genuchten Pc Model.

* * * * *